(12) United States Patent  
Botvinick et al.

(10) Patent No.: US 10,149,640 B2  
(45) Date of Patent: Dec. 11, 2018

(54) MEASURING OXYGEN LEVELS IN AN IMPLANT, AND IMPLANTS HAVING INCORPORATED OXYGEN SENSING

(71) Applicant: The Regents of the University of California, Oakland, CA (US)

(72) Inventors: Elliot Botvinick, Irvine, CA (US); John Weidling, Long Beach, CA (US)

(73) Assignee: The Regents of the University of California, Oakland, CA (US)

( * ) Notice: Subject to any disclaimer, the term of this patent is extended or adjusted under 35 U.S.C. 154(b) by 423 days.

(21) Appl. No.: 14/739,912

(22) Filed: Jun. 15, 2015

(65) Prior Publication Data

US 2015/0359472 A1 Dec. 17, 2015

Related U.S. Application Data

(60) Provisional application No. 62/012,906, filed on Jun. 16, 2014.

(51) Int. Cl.
```
A61B 5/1455    (2006.01)
A61B 5/1459    (2006.01)
A61B 5/00      (2006.01)
A61B 5/01      (2006.01)
A61B 5/145     (2006.01)
```

(52) U.S. Cl.
CPC ........ *A61B 5/14556* (2013.01); *A61B 5/1459* (2013.01); *A61B 5/14552* (2013.01); *A61B 5/686* (2013.01); *A61B 5/01* (2013.01); *A61B 5/14539* (2013.01); *A61B 2503/40* (2013.01)

(58) Field of Classification Search
None
See application file for complete search history.

(56) References Cited

U.S. PATENT DOCUMENTS

| | | | | |
|---|---|---|---|---|
| 2009/0075321 A1* | 3/2009 | Obeid | ............... | A61B 5/14542 435/29 |
| 2009/0216097 A1* | 8/2009 | Wilson | ............... | A61B 5/14539 600/327 |
| 2012/0016217 A1* | 1/2012 | Srivastava | ........... | A61B 5/0071 600/317 |

FOREIGN PATENT DOCUMENTS

WO   WO2014197798 A2   12/2014

OTHER PUBLICATIONS

Baleizao, Carlos, et al. "Dual fluorescence sensor for trace oxygen and temperature with unmatched range and sensitivity." Analytical chemistry 80.16 (2008): 6449-6457.
Liebsch, Gregor, et al. "Luminescence lifetime imaging of oxygen, pH, and carbon dioxide distribution using optical sensors." Applied Spectroscopy 54.4 (2000): 548-559.
Wolfbeis, Otto S., et al., "Fiber-optic fluorosensor for oxygen and carbon dioxide." Analytical chemistry 60.19 (1988): 2028-2030.

(Continued)

*Primary Examiner* — Eric Winakur  
*Assistant Examiner* — Marjan Fardanesh  
(74) *Attorney, Agent, or Firm* — Nguyen & Tarbet Law Firm

(57) ABSTRACT

Disclosed herein are embodiments of methods and techniques for measuring oxygen levels of an implant. The implant can have a plurality of oxygen-sensitive microparticles incorporated throughout. The oxygen-sensitive microparticles can receive light and emit excitation light in response. The levels of excitation light emitted can be directly related to oxygen concentration in the implant.

20 Claims, 14 Drawing Sheets

(56) References Cited

OTHER PUBLICATIONS

Borisov, Sergey M., Roman Seifner, and Ingo Klimant. "A novel planar optical sensor for simultaneous monitoring of oxygen, carbon dioxide, pH and temperature." Analytical and bioanalytical chemistry 400.8 (2011): 2463-2474.
Ching CD et al. A reliable method for isolation of viable porcine islets. Arch Surg 136: 276-279, 2001.
Thanos CG and Elliot RB. Encapsulated porcine islet transplantation: an evolving therapy for the treatment of Type I diabetes. Expert Opin Biol Ther. 9(1):29-44. 2009.
Sutherland D, et al. Isolation of human and porcine islets of Langerhans and islet transplantation in pigs. Journal of Surgical Research. 16(2): 102-111. 1974.
Larsen M and Rolin B. Use of the Gottingen Minipig as a Model of Diabetes, with Special Focus on Type 1 Diabetes Research. ILAR Journal. 45(3):903-313. 2004.
Korbutt GS, et al. Neonatal porcine islets as a possible source of tissue for humans and microencapsulation improves the metabolic response of islet graft post transplantation. Ann N Y Acad Sci. 831:294-903. 1997.
Lamb M et al. In vitro maturation of viable islets from partially digested young pig pancreas. Cell Transplant. Feb. 7, 2013.
Kuehn C et al. Young porcine endocrine pancreatic islets cultured in fibrin show improved resistance toward hydrogen peroxide. Islets. Nov. 21, 2013;5(5).
Darrabie MD et al. Characteristics of poly-L-ornithine-coated alginate microcapsules. Biomaterials 26/34: 6846-6852, 2005.
De Vos P, et al. Multi scale requirements for bioencapsulation in medicine and biotechnology. Biomaterials. 90:2559-2570. 2009.
Schrezenmeir J. et al. Long-Term Function of Porcine Islets and Single Cells Embedded in Barium-Alginate Matrix. Horm Metab Res 1993; 25(4): 204-209.
Chowdary K et al. Evaluation of Olibanum Resin as a new microencapsulating agent for Aceclofenac Controlled Release Microcapsules. Research Journal of Pharmaceutical, Biological and Chemical 2011; 2(1) 0975-8585.

Fehsel K et al. Necrosis is the predominant type of islet cell death during development of insulin-dependent diabetes mellitus in BB rats. 2003; 83(4):549-59.
Chang N et al. Direct Measurement of Wound and Tissue Oxygen Tension in Postoperative Patients. Annals of Surgery 197(4): 470-478.1983.
Spokane RB. et al. An implanted peritoneal oxygen tonometer that can be calibrated in situ. ASAIO Transactions. 36 (3): M719-M722. 1990.
Schrenzenmeir J et al. Effect of microencapsulation on oxygen distribution in islet organs. Transplantation, 57 (1994).
Michiels C. Physiological and pathological responses to hypoxia. (2004) 164(6): 1875-1882.
Veriter S, et al. In vivo selection of biocompatible alginates for islet encapsulation and subcutaneous transplantation. Tissue Eng Part A. 16(5):1503-1513. 2010.
Quaranta, Michela, Sergey M. Borisov, and Ingo Klimant. "Indicators for optical oxygen sensors." Bioanalytical reviews 4.2-4 (2012): 115-157.
Borisov SM et al. Phosphorescent Platinum (II) and Palladium (II) Complexes with Azatetrabenzoporphyrins—New Red Laser Diode-Compatible Indicators for Optical Oxygen Sensing. ACS Appl Mater Interfaces. Feb. 24, 2010; 2 (2): 366-374.
Carraway, E. R.; Demas, J. N.; Degraff, B. A.; Bacon, J. R. Anal. Chem. 1991, 63, 337-342.
Ladurner, Ruth, et al. "Predictive value of routine transcutaneous tissue oxygen tension (tcpO2) measurement for the risk of non-healing and amputation in diabetic foot ulcer patients with non-palpable pedal pulses." Med Sci Monit 16.6 (2010): 273-277.
De Backer, Daniel, et al. "Monitoring the microcirculation in the critically ill patient: current methods and future approaches." Applied Physiology in Intensive Care Medicine 2. Springer Berlin Heidelberg, 2012. 263-275.
Schrezenmeir, J et al. The role of oxygen supply in islet transplantation. Transp. Proc. 24(6): 2925-2929. 1992.

\* cited by examiner

MEASURING OXYGEN LEVELS IN AN IMPLANT, AND IMPLANTS HAVING INCORPORATED OXYGEN SENSING

STATEMENT REGARDING FEDERALLY SPONSORED R&D

This disclosure was made with government support under grant FA9550-10-1-0538 awarded by the Air Force Office of Scientific Research and grant P41EB015890 awarded by the National Institutes of Health. The government has certain rights in the disclosure.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

This disclosure relates generally to monitoring conditions like oxygen concentration, pH, and temperature in and around implants in patients.

SUMMARY OF THE INVENTION

Disclosed herein are embodiments of an implantable system for tissue the system comprising an implant configured to be inserted into the tissue, and a plurality of oxygen-sensitive microparticles incorporated into the implant, the microparticles comprising a polymer or natural matrix and a radiation-sensitive dye embedded within the polymer matrix, wherein the radiation-sensitive dye is configured to emit an emission radiation upon excitation by a radiation source, wherein an intensity, a lifetime, or an intensity and a lifetime of the emission radiation correlates with oxygen levels within the implant.

In some embodiments, the implant may not be tethered outside of the tissue.

In some embodiments, the implant can comprise a polymer. In some embodiments, the radiation-sensitive dye can comprise porphyrin dye or a metalloporphyrin dye. In some embodiments, the radiation-sensitive dye can be selected from the group consisting of platinum (II) meso-tetraphenyl tetrabenzoporphine and platinum (II) meso-tetra(pentafluorophenyl)porphine. In some embodiments, the polymer matrix can comprise a polystyrene matrix. In some embodiments, the radiation sensitive dye can be configured to interact with oxygen within the implant thereby quenching the emission radiation.

In some embodiments, the implant can comprise a portion made of a permeable material and the oxygen-sensitive microparticles are incorporated into the permeable material. In some embodiments, the implant can comprise fluidic channels and the oxygen-sensitive microparticles are incorporated into the fluidic channels. In some embodiments, the implant can comprise fluidic channels and the oxygen-sensitive microparticles are incorporated into the implant but not in the fluidic channels.

In some embodiments, the implant can contain cells. In some embodiments, the cells can be encapsulated islet cells.

In some embodiments, the tissue can be selected from the group consisting of patient tissue, animal tissue, plant tissue, and microbe culture.

Also disclosed herein are embodiments of a method of determining an oxygen concentration within an implant, the method comprising deploying the implant within a patient, the implant comprising a plurality of oxygen-sensitive microparticles comprising a polymer matrix and a radiation-sensitive dye embedded within the polymer matrix, wherein the radiation-sensitive dye is configured to emit an emission radiation upon excitation by a radiation source, wherein an intensity, a lifetime, or an intensity and a lifetime of the emission radiation correlates with the oxygen concentration within the implant, irradiating the implant to excite the radiation-sensitive dye causing the radiation-sensitive dye to emit the emission radiation, detecting the intensity, the lifetime, or the intensity and the lifetime of the emission radiation, and determining the oxygen concentration within the implant based on the correlation between the emission radiation and the oxygen concentration.

In some embodiments, the oxygen concentration is determined continuously. In some embodiments, the oxygen concentration is determined intermittently. In some embodiments, the radiation-sensitive dye is selected from the group consisting of platinum (II) meso-tetraphenyl tetrabenzoporphine and platinum (II) meso-tetra(pentafluorophenyl)porphine.

Also disclosed herein are embodiments of a sensor system for determining oxygen concentration within an implant, the system comprising an implant configured to be deployed into a patient, the implant having a plurality of oxygen-sensitive microparticles incorporated within, each of the plurality of oxygen-sensitive microparticles comprising a polymer matrix and a radiation-sensitive dye embedded within the polymer matrix, wherein the radiation-sensitive dye is configured to emit an emission radiation upon excitation by a radiation source, and an electro-optical probe configured to excite the oxygen-sensitive microparticles and detect the emission radiation from the radiation-sensitive dye, wherein an intensity, a lifetime, or an intensity and a lifetime of the emission radiation correlates with oxygen levels within the implant.

In some embodiments, the radiation-sensitive dye comprises metalloporphyrin dye. In some embodiments, the electro-optical probe is located on the patient's skin, or near the patient's skin.

BRIEF DESCRIPTION OF THE DRAWINGS

FIG. 2C an embodiment of an optical probe which can be used for in vivo measurements.

DETAILED DESCRIPTION

Figure 1:
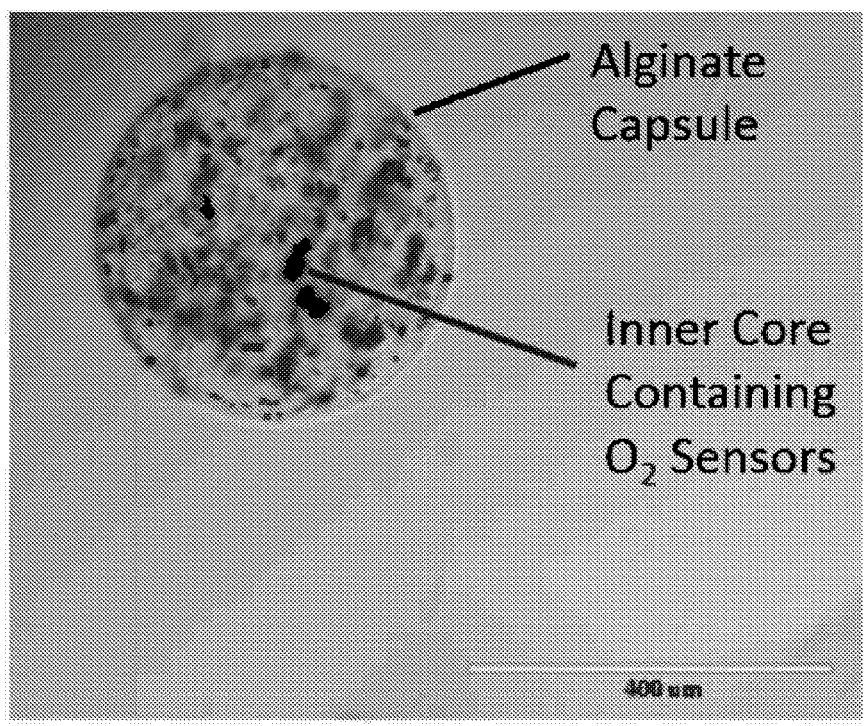
FIG. 1 shows alginate capsule device containing an embodiment of an OSM sensors.

Disclosed herein are embodiments of microparticles and dyes for continuously measuring oxygen concentrations inside an implant, such as an implantable device, as well as methods of forming the implant having the oxygen sensitive microparticles and/or dyes incorporated within. Thus, the particular oxygen content can be measured within the implant itself, a significant improvement over the current state of oxygen measurement systems. Specifically, to make inner implant oxygen measurements, disclosed herein are embodiments of methods to incorporate oxygen sensitive dyes into the implant material so that the oxygen level can be measured from outside the body with light. While oxygen concentrations are specifically discussed, it will be noted that other environmental conditions, such as pH, $CO_2$ levels, and temperature can also be measured.

One of the great challenges for creating a successful non-autologous cellular therapy is to provide the new cells in the body with sufficient oxygen and nutrient transfer to survive while protecting them from the immune system. An array of techniques for encapsulating islet cells in alginate have been studied and tested extensively, but ultimately fail within weeks due to, in part, hypoxic conditions.

Cellular therapies and certain tissue transplants hold promise to replace the implantation of whole organs in the treatment of disease. For most cell types, in vivo viability depends on oxygen delivery to avoid toxic effects of hypoxia. A promising approach is the in situ vascularization of implantable devices which can mediate hypoxia and improve both the lifetime and utility of implanted cells and tissues. While mathematical models and bulk measurements of oxygenation in surrounding tissue have been used to estimate oxygenation within devices, such estimates are insufficient in determining if supplied oxygen is sufficient for the entire thickness of the implanted cells and tissues.

Previously, tissue $pO_2$ measurements have been taken at the implant site at different time points after the device has been implanted to see whether the oxygen level around the implant is increasing or decreasing. These measurements around the area of the implant may be useful for determining the amount of vascularization around the device, but these measurements may not tell us what the oxygen level is inside the implant. It can be advantageous to know the oxygen level inside the implant because eventually there will be cells loaded inside the implant that will need a certain amount of oxygen to survive. Knowing the amount of oxygen in the implant at different time points may help determine whether or not the implant itself, or the way it is implanted, is providing sufficient oxygen for cell survival. Thus, embodiments of the disclosure allow a user to determine the oxygen levels within an implant.

There are devices for measuring $pO_2$ levels around the implant but no systems would be able to measure the level of oxygen inside embodiments of the disclosed implant. For example, optical oxygen sensing using luminescent dyes has gained popularity and is used in some commercial fiber-based optical oxygen probes, such as the Ocean Optics NeoFox system, and the PreSens Oxygen Probes (which can be used in biological applications). These devices show that the luminescence-based sensing of oxygen is reliable, but they fall short of being able to measure within implanted materials on small scales and would require a tethered component crossing the skin surface.

Other technologies exist to measure oxygen levels proximal to an implant non-invasively, but these technologies do not measure oxygen within the device and thus cannot report on the microenvironment of encapsulated tissues. Such technologies include oxygen electrodes either implanted or in contact with skin, or scattered light methods such as diffuse optical spectroscopy ($SpO_2$ measurement) and NIR spectroscopy.

OSM Description and Use

Disclosed herein are embodiments of techniques for measuring the oxygen concentration continuously inside an implanted object such as, for example, an alginate bead, an islet suspension device, an artificial pancreas, or a glucose sensor, though other the particular type of implant is not limiting.

Other such implants include macrodevices for encapsulation of cells, vascularized implant devices, vascular stents, heart valves, subcutaneous drug eluding devices, polymer fillers, skin grafts, artificial skin, wound treatments. In general, devices that promote integration with the surrounding tissue where oxygenation within the device must be monitored can be used with embodiments of the disclosure. Further, the techniques can be used to measure oxygen concentrations in animal tissue, plants, and microbe cultures.

Specifically, disclosed herein are embodiments for the direct measurement of oxygen partial pressures within such implanted devices. The disclosed sensors can comprise oxygen-sensitive microparticles (OSMs) and an electro-optical probe to noninvasively, or invasively, excite OSMs and record emitted light from which $pO_2$ can be determined. In some embodiments, the probe can be placed near a patient's skin to irradiate the OSMs and receive their emitted light. In some embodiments, the probe can be placed on a patient's skin to irradiate the OSMs and receive their emitted light. Additionally, disclosed herein is a protocol to measure both the steady state $pO_2$ within devices as well as transport dynamics between the device and the local vasculature.

Embodiments of the disclosed sensor can have oxygen-sensitive microparticles (OSMs) incorporated into the volume of subcutaneously implantable devices, such as those mentioned above. Oxygen partial pressure within these devices can be measured directly in vivo by an optical probe placed on the skin surface so that light, or radiation, from the optical probe is emitted towards the OSMs.

In some embodiments, OSMs can be made from an oxygen-sensitive dye embedded within a polystyrene matrix. However, other polymer matrices can be used as well, and the particular matrix is not limiting.

As validation, OSMs have been incorporated into alginate beads, commonly used as immunoisolation devices to encapsulate pancreatic islet cells. Alginate beads were implanted into the subcutaneous space of Sprague-Dawley rats. Oxygen transport through beads was characterized from dynamic OSM signals in response to changes in inhaled oxygen. Changes in oxygen dynamics over days demonstrate the utility of our technology. A further discussion of this can be found below.

In some embodiments, the OSMs contain a reporting agent that is a light-sensitive reagent and can include, for example, porphyrin dyes (i.e. platinum tetrabenzo porphyrin), and this porphyrin dye may be used on the sensor. Light, or other radiation, can be emitted from a diode, or other radiation source such as a laser or heater, and then absorbed by a light sensitive dye. The light-sensitive dye is excited by the light source and the light-sensitive dye emits its own radiation, such as fluorescence.

In some embodiments, the dye can emit a fluorescent signal which can be detected by a sensor. The fluorescent lifetime of the dye can be quenched (e.g. lowered) where more oxygen is present, which can allow for determining the level of perfusion of the device. As the patient can inhale gas with different oxygen compositions (e.g., 100% $O_2$, 80% $O_2$, 60% $O_2$), the rate at which the dye reacts to changes in inhaled gas can correlate with the amount the device is perfused. The quicker the reaction of the dye to changes in inhaled gas indicates a well perfused device, as vasculature carries the gas inhaled, and the more vasculature running through the implant, the quicker the inhaled gas is carried to the implant.

As mentioned, oxygen may interact with, for example bind with, the light-sensitive dye, thereby quenching fluorescence emissions, thus reducing the intensity and/or decay time of the light. Further, the oxygen can cause, and thus be correlated with, other time-sensitive metrics as well. The fluorescence emitted by the excited porphyrin dye can be collected on a photodetector, potentially through the optical probe, and the intensity and/or decay time of the emitted light can be measured and can be related to the oxygen concentration through a known calibration. For example, the optical data can be sent through a computer, processor, tablet, smartphone, or other device that can translate the optical data to readable data for a user.

In some embodiments, the probe can be used to continuously read the concentration of oxygen over time. In some embodiments, the probe can be used to make intermittent measurements as desired by a user, such as every minute, hour, or day, though the particular interval is not limiting.

In some embodiments, the calculated concentration of oxygen from the probe can be sent to a display where the user can interface with the device. The display can be, for example, a video screen, computer screen, mobile device, or tablet, but the particular display is not limiting. In some embodiments, the display can provide for real-time data.

Following is a list of dyes that could be used for embodiments of the disclosed sensor: metalloporphyrins such as PtOEP, PdOEP, PtTFPP, PdTFPP, PtOEPK, PdOEPK, PtTFPPL, PdTFPPL, PtTPTBP, PdTPTBP, PtTPTBPF, PdTPTBPF, Pt1NF, Pd1NF, Pt2NF, Pd2NF, Pt3NF, Pd3NF, PtTPTNP, PdTPTNP, PtTBP(CO2Bu)8, PdTBP(CO2Bu)8, PtNTBP, PdNTBP, Oxyphor R2, Oxyphor G2, PtTCPP. Additional dyes include but are not limited to cyclometallated complexes such as Ir(III) or Pt(II): Ir(ppy)3, Ir(ppy-NPh2)3, Ir(btpy)3. Additionally, transition metals polypyridyl complexes such as [Ru(bpy)3]2+, [Ru(dpp)3]2+ may also be used as dyes to measure oxygen concentration.

Following is a list of dyes that allow for the lifetime measurement of temperature which could be used be embodiments of the disclosed sensor, the dyes include, but are not limited to, the following:
ruthenium tris-1,10-phenanthroline in a poly(acrylo-nitrile) matrix
Ruthenium(II)-tris-(1,10-phenanthroline)-hexafluorophosphate in a poly(acrylo-nitrile) matrix Following is a list of dyes that allow for the measurement of $CO_2$ which could be used in embodiments of the disclosed sensor and include, but are not limited to, the following:
Ruthenium(II)-tris-(4,4 9-diphenyl-2,2 9-bipyridyl)-trimethylsilylpropansulfonate. +m-cresolpurple (donor and acceptor dye) in an ethyl cellulose matrix
1-hydroxypyrene-3,6,8-trisulfonate
8-hydroxy-pyrene-1,3,6-trisulfonate and tetraoctylammonium cation (HPTS(TOA)3) with TOAOH in an ethyl cellulose matrix Following is a list of dyes that allow for the measurement of pH which could be used in embodiments of the disclosed sensor and include, but are not limited to, the following:
Ruthenium(II)-tris-(4,4 9-diphenyl-2,2 9-bipyridyl)-trimethylsilylpropansulfonate+bromthymolblue (donor and acceptor dye) in a polyurethane matrix Thus, as shown above, different physiological measurements other than oxygen can be taken inside of an implant, and the particular measurement is not limiting.

There can be numerous methods for incorporating the OSMs into the implant, and no particular methodology is limiting. For example, in some embodiments the dye can be mixed with alginate or other permeable materials such as Polyethylene Glycol (PEG), polylactic-co-glycolic acid) (PLGA), fibrin, collagen, Hyaluronan (HA), or Hydroxyethylmethacrylate (HEMA), etc) which can form into beads which contain the dye. These beads can be incorporated into a permeable implant, for example during the manufacturing process, and thus the implant will be imbedded with a number of OSMs.

Another way to incorporate the oxygen-sensitive dye into an implant is to load the oxygen sensitive particles into fluidic channels formed in certain implants configured to support vascularization of cells transplanted into fluidic channels within the implants; see e.g., Int'l. Pat. App. No. WO 2014/197798, incorporated herein in its entirety. The channels of the implant will eventually be loaded with cells such as islets, so measuring the oxygen levels within the channels will provide an even more accurate measurement of the oxygen level that the cells will experience. This can be done during the manufacturing of the implant, or after the implant is fully finished. For example, in some embodiments the dye can be added with the cells into the fluidic channel of the device. Upon determination of the perfusion of the implant, it can be determined when the channels are an ideal environment for cells to be housed, and thus cells can be introduced.

In some embodiments, the oxygen-sensitive dyes can be incorporated by integrating them within materials comprising the device, and not designated channels within. This can be done, for example, during the manufacturing of the implant. For example, as described in below, the dye can be integrated into HEMA, which can be cast or printed into 2D or 3D devices in which the dye is contained within the walls of the device. The dyes can also be incorporated into a thin layer coating surfaces of the device, for example the outer surface or inner features. Therefore, in some embodiments the OSMs may not be used and the dye can be directly incorporated into the implant.

Experiments, discussed below, were performed on an alginate bead, and its operation was verified in vivo in rats by measuring its response to changing inhaled oxygen concentrations and comparing that response at two time points within the first week of implantation, during which wound healing is most active. The results showed that embodiments of the disclosed techniques track changes in oxygen in implanted alginate beads and that the rate of oxygen transfer to the implanted beads increased during the wound healing process. This link between wound healing and oxygen transport dynamics within the implanted microbeads could have implications for identifying designs that lead to either cell survival or cell death. By knowing the amount of oxygen inside the implants one may be able to correlate that level with critical points in the wound healing process, such as new vessel formation or the identification of areas that have become 'walled-off' from the body.

Accordingly, embodiments of the disclosure have been demonstrated to continuously measure $pO_2$ within implanted alginate microbeads, as a representative example of an implant though other implants could be used as well and optically interrogated using inexpensive optical components coupled to a data acquisition device, such as those used in the art. Microbead $pO_2$ values measured subcutaneously in embodiments of the disclosure (~45-120 mmHg) were higher than those reported by Veriter and colleagues (~5-40 mmHg) where larger alginate devices were implanted in a similar manner. This difference can be attributed to differential tissue responses or the accuracy of the sensor. Likely it is due to differential tissue response because it is known that alginate microbeads elicit a moderate tissue response as compared to a slab.

Embodiments of the disclosure calibrated against known gases had a regression coefficient of $R^2 > 0.99$ indicating the accuracy of our system.

In some embodiments, there may be no delay in determining oxygen levels from the implant. In some embodiments, there may be a partially delay in determining oxygen levels in the implant. For example, there are four time scales: (1) the decay time of the dyes in microseconds, (2) the time is takes to compute the oxygen pressure (3) the period between measurements, dictated by the user, (4) the oxygen dynamics between changes in blood and tissue oxygen when inhaled gas is exchanged from one oxygen pressure to another. Time scale 3 is determined by the user while 1 and 4 are not. Time scale 2 is a function of how quickly the light emitted from the dye is analyzed. The decay can be fit to an exponential that is computationally quick. In some embodiments, light intensity can be used, which is faster to compute, but may have some disadvantages as changes in intensity are very sensitive to factors other than oxygen, for example movement. Further, an autocorrelation function can be calculated, which is computationally expensive. However all of these computation times are very fast compared to the time scales of physiology. Further, in some embodiments, encapsulated islet cells can be added to implants having the disclosed sensor, such as those described in Int'l. Pat. App. No. WO 2014/197798, hereby incorporated by reference in its entirety, and measured oxygen levels can be correlated with implant functionality and cell survival. This will lead to a better understanding of the role of oxygen in implanted devices.

Need Related to Treatment of Diabetes

Non-autologous tissue transplantation is a promising approach to overcome the scarcity of human pancreas donor tissue in treatment of type 1 diabetes. To this end, a scalable Islet of Langerhans (islet) isolation method has been developed wherein partially digested piglet pancreatic tissue is matured in vitro over 8-days by incubation in a novel cell culture media. During this period exocrine tissue dies and isolated islets remain, which have shown to be responsive to glucose challenges. Isolated islets can be encapsulated within permeable hydrogels, such as alginate, to provide an immuno-protective barrier that may preclude pharmacological immunosuppression. Piglet islets may be isolated and encapsulated within permeable hydrogels such as alginate to provide an immuno-protective barrier that may preclude pharmacological immunosuppression. However, encapsulation devices introduce a transport barrier between the host and graft tissues and inherently limits oxygen supply, compromising graft function and cell viability, problems that scales with device wall thickness.

Typically grafts are implanted in subcutaneous or intraperitoneal sites where partial pressures of oxygen ($pO_2$) are approximately 60 mmHg and 40 mmHg respectively, which is lower than arterial blood (>80 mmHg). It is commonly asserted that low cell viability within devices results from low tissue oxygen taken together with device diffusional barriers to create hypoxic and anoxic conditions, where these conditions are known to promote cell death through necrosis and apoptosis. However, direct measurement of oxygen levels within micro-encapsulated devices in vivo has not been previously reported, where such measurements are ultimately required to assay the efficacy of implant technologies that claim to promote oxygen delivery. In a study of relatively large alginate disc implants (1-1.5 $cm^2$ surface area at 3-6 mm thick), oxygen within implanted devices was directly measured through the use of electronic paramagnetic resonance (EPR) oximetry in rats. However, current research shows that such thick devices cannot retain islet function, likely due to diffusional limitations, thus promoting microencapsulation technologies such as thin sheets or microbeads of permeable materials.

Example

Disclosed below is a particular testing and set of example using the above-disclosed embodiments of a sensor.
Preparation of OSMs Two types of OSMs were fabricated, each comprising a unique oxygen-sensing metalloporphyrin dye discussed above. The first is Platinum (II) meso-Tetraphenyl Tetrabenzoporphine (PtTPTBP) and the second is Platinum (II) meso-tetra(pentafluorophenyl)porphine (PtTFPP). OSMs were fabricated by first mixing 2 mg dye with 30 mg of polystyrene ($M_w$ 2500) and then dissolving the mixture in 450 μl Chloroform. The solution was pipetted and spread onto a glass slide to polymerize overnight in room air at 23° C. The resulting thin film was scraped off with a razor blade and crushed into small micron-sized particles (2-20 μm) using a glass mortar and pestle.
Encapsulation of OSMs within Alginate Beads Clinical grade ultra-pure low viscosity alginate (UPLVM) was dissolved in deionized water at 3 wt % and sterile filtered using a 0.22 micron syringe filter. OSMs were suspended in 1.5 mL of the UPLVM solution and loaded into an encapsulator for the fabrication of alginate beads. Specifically, the solution was first loaded into a syringe and then driven through a 25 G needle under positive gas pressure (4 PSI, $N_2$). The needle was held at 9V relative to a 120 mM $CaCl_2$ solution within a Petri dish placed below the tip of the needle. Alginate beads formed at the tip of the needle and fell into the $CaCl_2$ solution for alginate polymerization. A typical OSM alginate bead is shown in FIG. 1. Bead size is dependent on gas pressure, voltage and distance between the needle and media in the dish. For these experiments, the average diameter of alginate beads was found to be 415±47.68 μm.

Figure 2A:
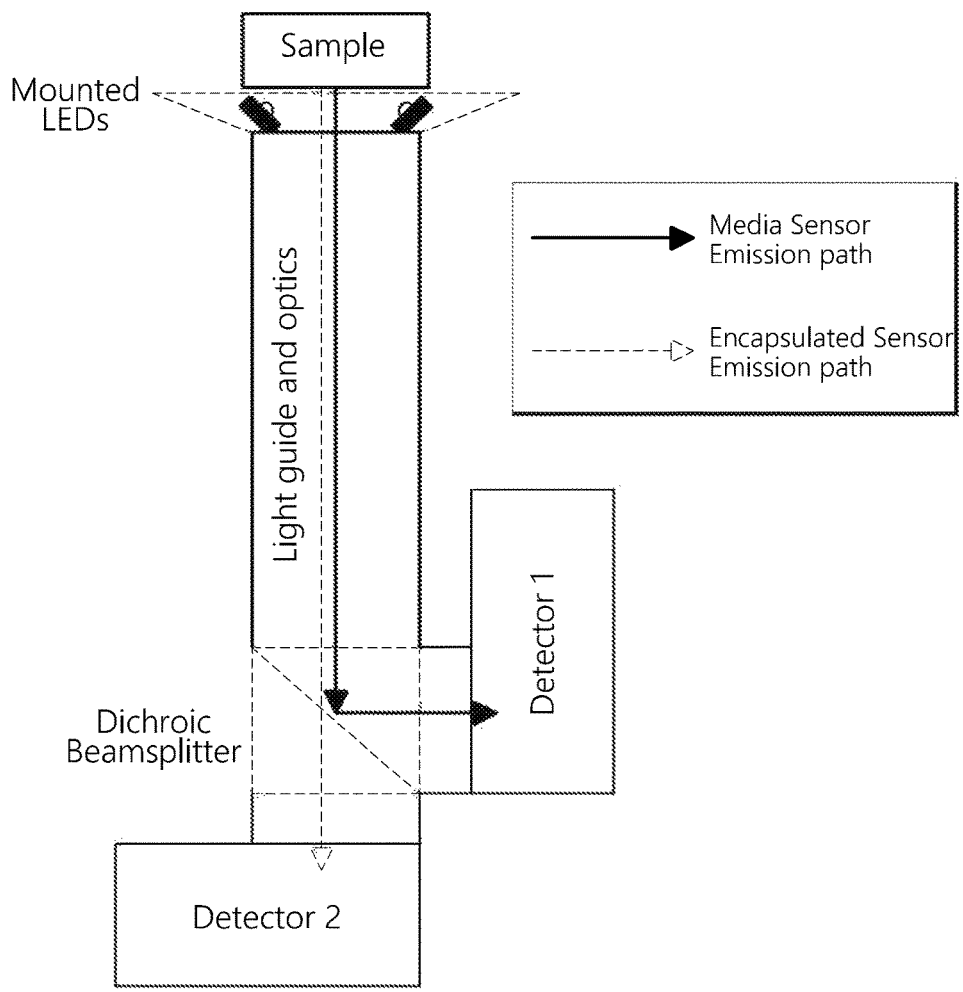
FIG. 2A illustrates an embodiment of an optical probe which can be used for in vitro measurements.
Figure 2B:
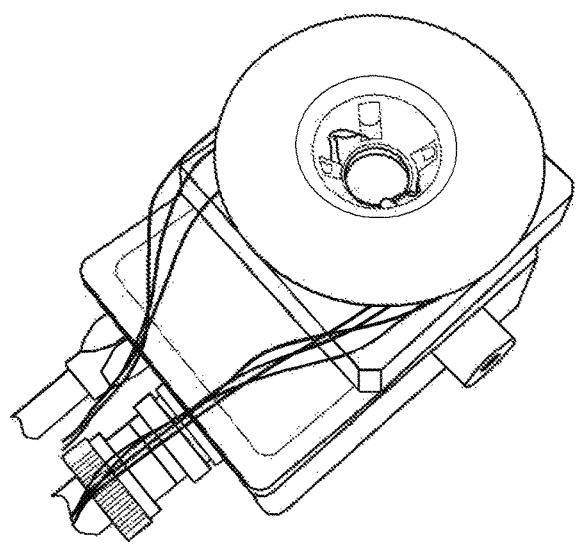
FIG. 2B illustrates a photograph of an embodiment of an optical probe which can be used for in vivo measurements.

Probing pO$_2$ within Alginate Beads Using an Optical Probe for In Vitro Experiments An optical probe was constructed to measure both OSM types simultaneously. A diagram of the optical probe is shown in FIGS. 2A-C. As shown in FIG. 2A, emitted light from two OSM types can be spectrally separated into two different detectors. In some embodiments, the probe can provide for 1, 2, 3, 4, 5 different wavelengths, though the amount of wavelengths is not limiting. Further, the optical probe can be configured to provide for different intensities.

The two OSM types can be separated spectrally. PtTFPP OSMs have multiple absorption peaks at 390 nm, 504 nm and 538 nm and emission peaks at 647 and 710 nm. PtTPTBP OSMs have multiple absorption peaks at 430 nm and 614 nm and an emission peak at 770 nm. Thus, the optical probe can selectively excite either type of OSM with two pairs of LEDs centered at 530 nm (green) and 617 nm (red) for PtTFPP and PtTPTBP respectively.

The LEDs were mounted onto a custom 3D printed conical mount designed to pitch the LEDs such that emitted light converges onto samples placed just above the surface of the cone. The conical mount was glued onto the distal surface of a 2" long lens tube containing a 6.4 mm diameter image conduit and a focusing lens (f=25 mm). The distal end of the lens tube was mounted onto a filter cube holder containing a long-pass dichroic beam splitter to reflect PtTFPP and transmit PtTPTBP emissions respectively. Two amplified photodiode detectors (9.8 mm diameter, Gain=30) were mounted onto the cube to detect emission from each OSM type. LED emission and digitalization of photodiode signals is conducted by a National Instruments data acquisition device controlled by LabView.

Determining Oxygen Partial Pressure from OSM Emission

OSMs were calibrated from measurements acquired at different pO$_2$ levels, as provided by four gas tanks containing different oxygen mixtures. OSM emission was analyzed using the method of luminescence lifetime. OSMs were optically excited by pulsing LED's in a 100 Hz squarewave with 50% duty cycle. Optical signals were sampled at 1 MHz. OSMs were probed every 20 seconds, where at each time point 25 measurements were acquired at 100 Hz and averaged. The metalloporphyrin dye within OSMs continues to emit light after the cessation of each LED light pulse. This emission can be modeled as an exponential decay as in equation 1:

$$V(t) = V_0 e^{\left(\frac{-t}{Tau}\right)} \quad \text{Equation 1}$$

where V is detector voltage, $V_0$ is voltage at the start of the decay, t is time, and Tau is the lifetime decay time constant. Dye emission was quenched by oxygen and consequently Tau decreases with increasing pO$_2$. The relationship between pO$_2$ and Tau can be described by a modified Stern-Volmer relationship:

$$\frac{Tau}{Tau_0} = \frac{f}{1 + K_{SV}[O_2]} + 1 - f \quad \text{Equation 2}$$

where Tau is oxygen-dependent lifetime decay time constant, $Tau_0$ is the zero oxygen lifetime decay constant, f is the fraction of emission of one site of a two-site model, and $K_{SV}$ is the Stern Volmer constant. $K_{SV}$ and f were estimated by optimization.

In Vitro Measurement of Oxygen Partial Pressure within Alginate Beads.

Figure 3A:
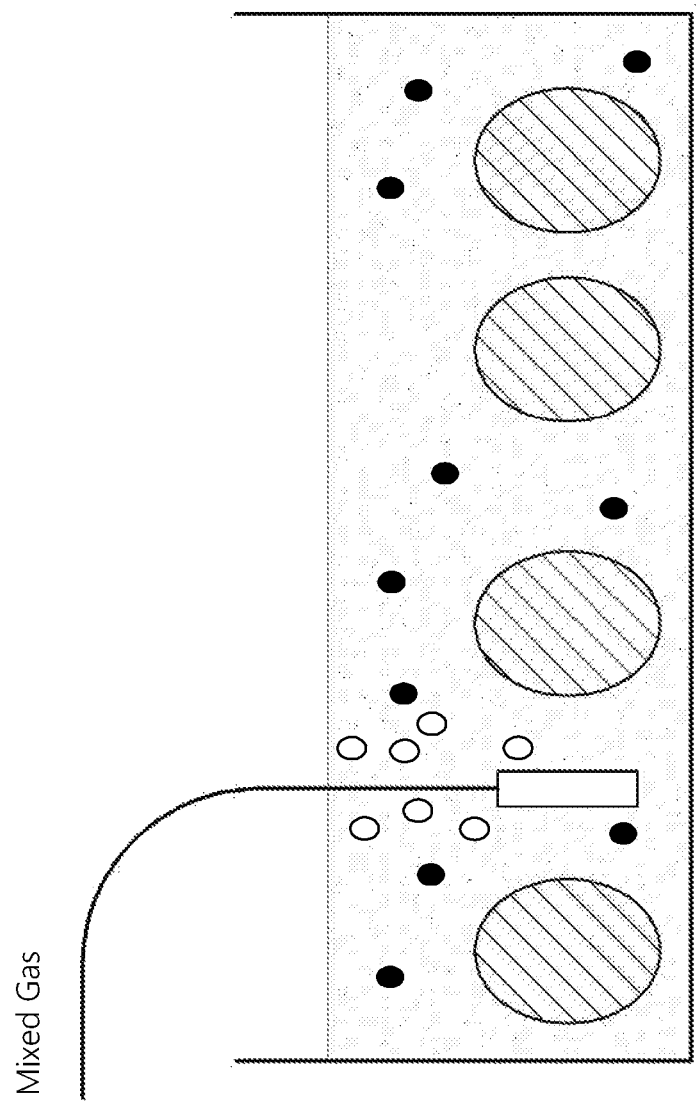
FIG. 3A illustrates an in vitro experiment where two spectrally distinct embodiments of OSM types are suspended in a PBS bath within a well.

Alginate beads containing PtTPTBP OSMs and un-encapsulated PtTFPP OSMs were suspended in 1 ml of media (PBS) within a single well of a 24-well dish (Corning) in which gas was bubbled (FIG. 3A) with either compressed air (21% oxygen), or precalibrated mixtures of 10% oxygen/ 90% Nitrogen, 5% oxygen/95% Nitrogen, and Argon gas (0% oxygen). As shown in FIG. 3A, a user can monitor PBS (filled in circles) and can monitor alginate capsules with imbedded OSMs (slashed circles).

Figure 3B:
FIG. 3B illustrates a close up view showing PBS and encapsulated OSMs within a well.

FIG. 3B is the actual set-up of the single well with varying gases bubbled through the solution. The grayscale image of FIG. 3B does not represent the two color particles.

Figure 4:
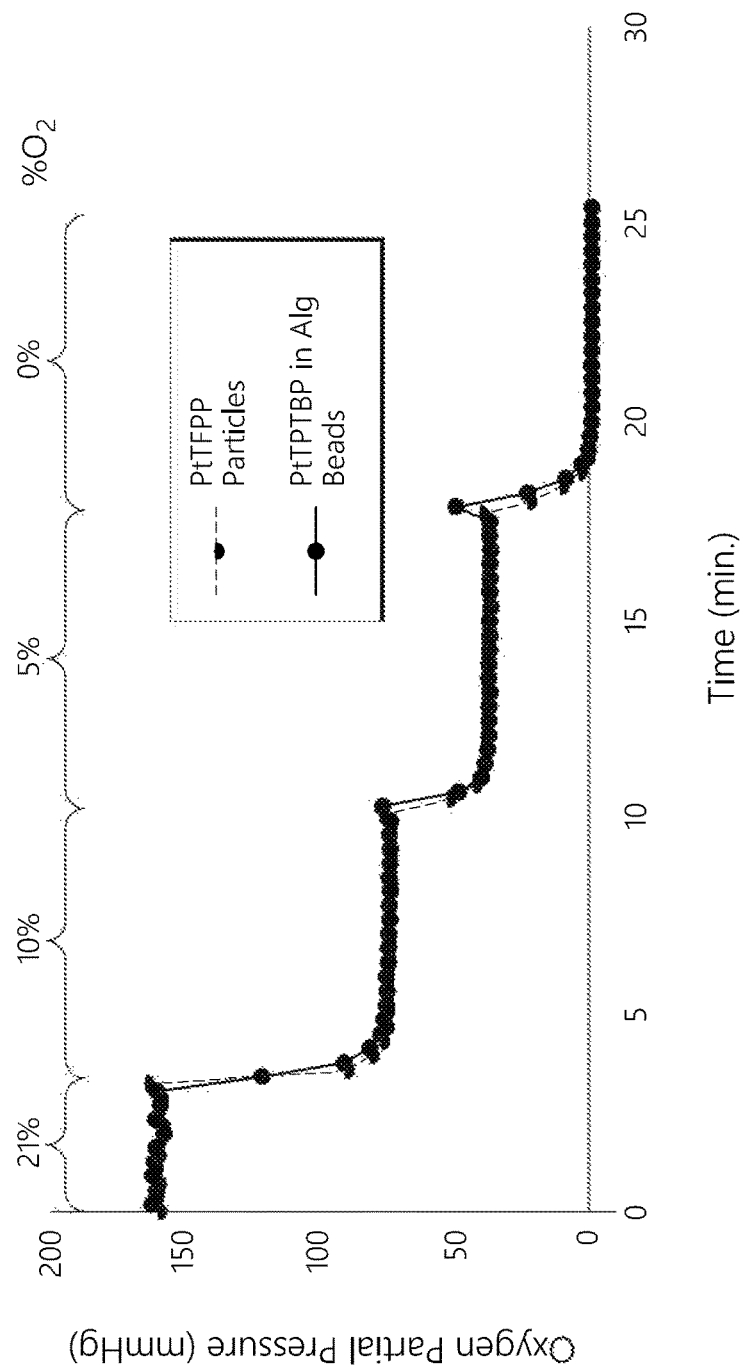
FIG. 4 illustrates in vitro measurements of $pO_2$ as reported by both the encapsulated and non-encapsulated OSMs vs. time for a series of gas exchanges.

FIG. 4 plots pO$_2$ as reported by both the encapsulated and non-encapsulated OSMs vs. time for a series of gas exchanges. The pO$_2$ levels were calculated by first computing the mean steady state lifetime values for each gas concentration using Equation 1. Regression of lifetime against gas concentration as computed by Equation 2 ($R^2$>0.99) provides a calibration equation mapping lifetime to pO$_2$. Data confirms oxygen sensitivity within the alginate bead and no significant dynamic delay between the PBS and the volume of the bead. As shown in FIG. 4, pO$_2$ for a set of gases containing oxygen at: 21%, 10%, 5%, and 0% where: dashed line: pO$_2$ in PBS; full line: pO$_2$ in capsules.

In Vivo Probe to Measure Oxygen Partial Pressure within Alginate Beads

A compact in vivo optical probe was constructed for PtTPTBP OSMs alone (FIG. 2B-2C). Since only one dye was being measured in vivo there was no need for the more complex optical setup used in the in vitro experiment. Two of the 617 nm-centered LEDs were mounted on the conical mount, as described above. The conical mount was then placed directly on the photodiode module and aligned with the active area of the photodiode. A 715 nm high-pass optical filter is mounted above the surface of the photodiode. The conical mount is placed directly onto the skin during measurements.

In Vivo pO$_2$

In vivo testing was performed to determine if PtTPTBP OSM signals can be related to pO$_2$ within subcutaneously implanted alginate beads. A small incision was made on the anterior side of an anesthetized rat. Anesthesia was maintained with a gas mixture of 100% oxygen and vaporized isoflurane delivered to a nose cone placed over the snout. OSM-containing beads were then implanted subcutaneously via pipette injection in a small pocket formed in the subcutaneous space by blunt dissection. The incision was closed using a wound sealing adhesive. pO$_2$ within beads was then optically probed on demand through the skin. Rats were fixed with a rodent pulse oximeter placed on the front paw to simultaneously measure oxygen saturation of blood hemoglobin (SpO$_2$) and heart rate. When averaging the 25 curves, variance at each point was found to be <0.5% of the mean value Equation. 1. In the absence of OSMs, the detector returns an exponential decay of Tau~15 μsec. To determine the weight of this effect on OSM-mediated signals, the mean signal value between 0 and 50 μsec of a OSM-mediated signals was divided by that for the OSM-free signals. The ratio was >7, which we found was insignificant for fitting OSM lifetimes.

Figure 5:
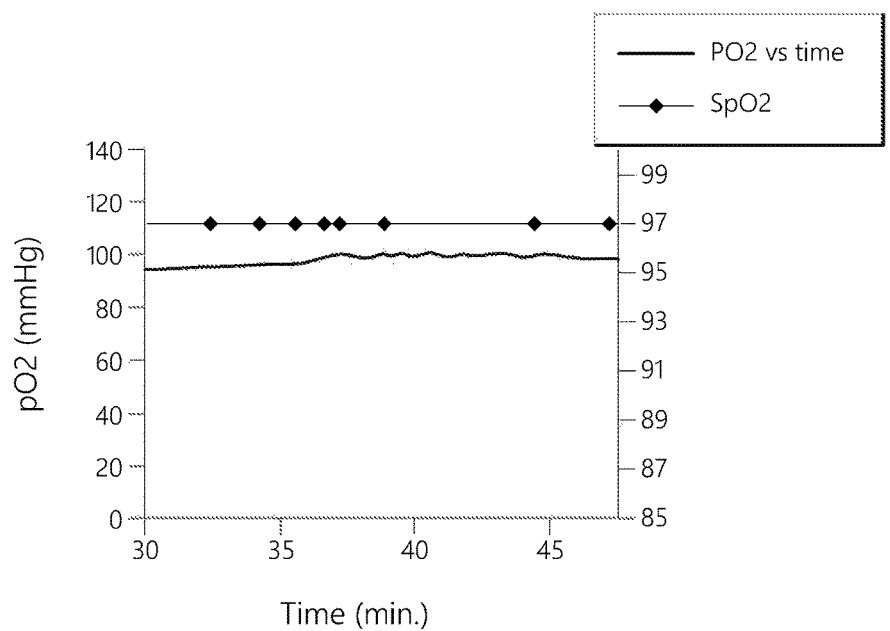
FIG. 5 illustrates day 5 $pO_2$ and $SpO_2$ for embodiments of a disclosed implant.

FIG. 5 shows pO$_2$ data acquired on day 5 post implantation during anesthesia. Animals were anesthetized during measurements with a mixture of isoflurane and 100% oxygen. As expected SpO$_2$ was constant at normal physiological levels (95-100%) at pO$_2$ within the beads was ~100 mmHg, indicating gas exchange both through the vasculature and skin.

The data collected in vivo was analyzed for its accuracy. Decay curves were collected as described above (measurements taken every 10 seconds with 25 curves for each measurement). When averaging the 25 curves, variance at each point was found to be <0.5% of the mean value (Eq. 1). In the absence of OSMs, the detector returns an exponential decay of Tau~15 μsec. To determine the weight of this effect on OSM-mediated signals, the mean signal value between 0 and 50 μsec of OSM-mediated signals was divided by that for the OSM-free signals. The ratio was >7, which we found was insignificant for fitting OSM lifetimes.

In Vivo Variable Inhaled Gas Experiment

Further disclosed herein are embodiments of an assay to measure transport dynamics between the microbeads and local vasculature. Such an assay can be advantageous since it captures effects of both increase/decrease of local vasculature resulting from the implantation wound and subsequent healing as well as the deposition of new collagenous tissue, which forms an additional diffusional barrier. Inhaled gas is rapidly changed as pO$_2$ and SpO$_2$ are monitored. Oxygen dynamics after each gas change are governed by tissue architecture, with rise/fall times increasing or decreasing as the local tissue rejects or perfuses the implant respectively.

For these tests using embodiments of the disclosed sensor, the 100% oxygen+isoflurane inhaled gas was transiently exchanged with room air (21% oxygen)+isoflurane and then returned to 100% oxygen+isoflurane. OSMs were probed every 10 seconds. Measurements were recorded on days five and nine post implantation.

Figure 6:
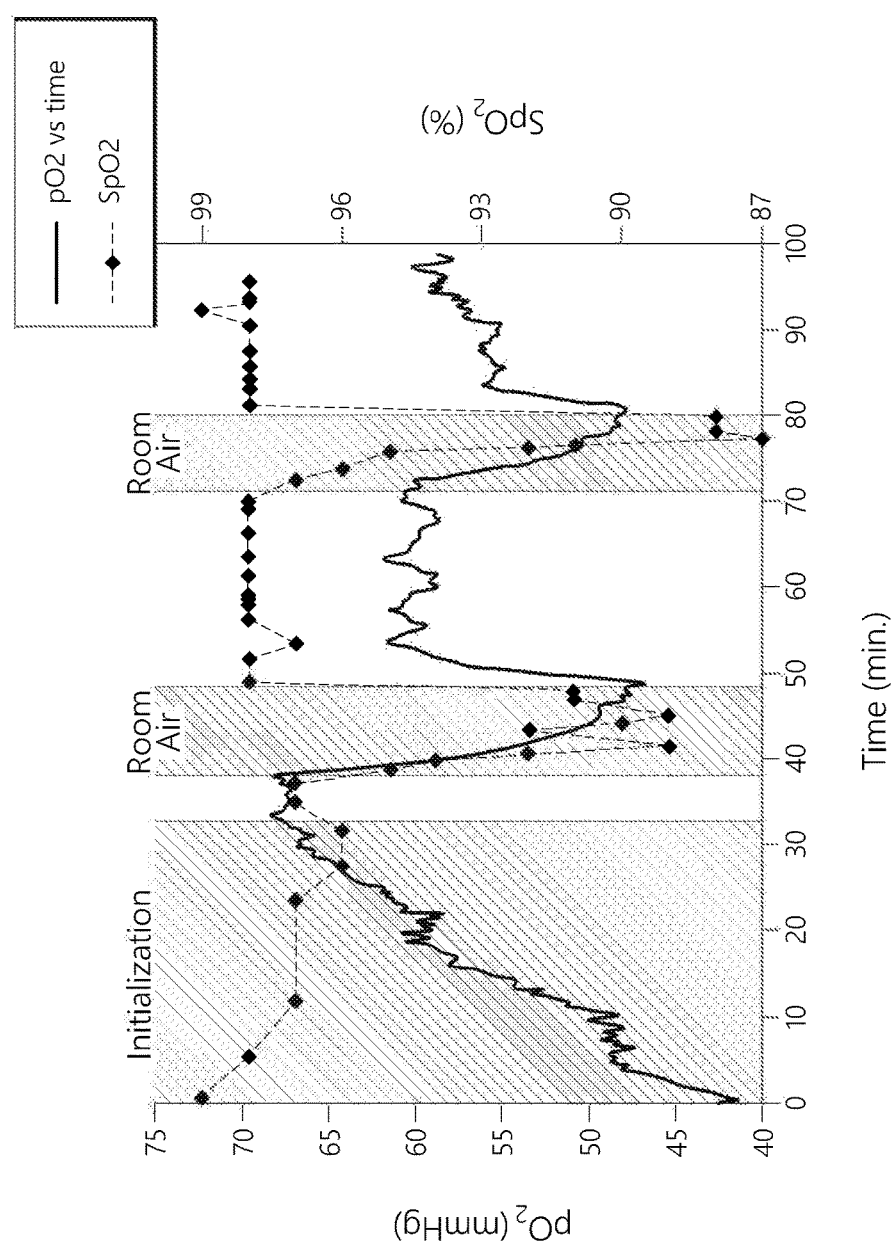
FIG. 6 illustrates variable inhaled gas experiment for embodiments of a disclosed implant.

FIG. 6 shows a typical variable inhaled gas experiment at day 5. pO$_2$ and SpO$_2$ exhibited dynamics in the early stages of anesthesia (first 30 minutes) and eventually reached a steady when breathing the 100% gas mixture. This phenomena was common to most experiments and is likely due to the physiological effects of isoflurane. The gas was changed to the room air mixture for ~10 minutes and then returned to the 100% O2 mixture for ~25 min. pO$_2$ within beads did not reach steady state within the 10 minutes of room air, but did within the 25 min of 100% O$_2$. Similar results were observed for the second room air challenge beginning at ~72 minutes.

On day 5, SpO$_2$ and pO$_2$ within capsules consistently exhibit dynamics after the initiation of anesthesia, stabilizing after approximately 30 minutes. At 37 minutes the percent oxygen mixed with isoflurane was changed from 100% to 21% for 11 minutes and then switched back. The same exchange in inhaled gas is repeated 26 minutes later.

Figure 7:
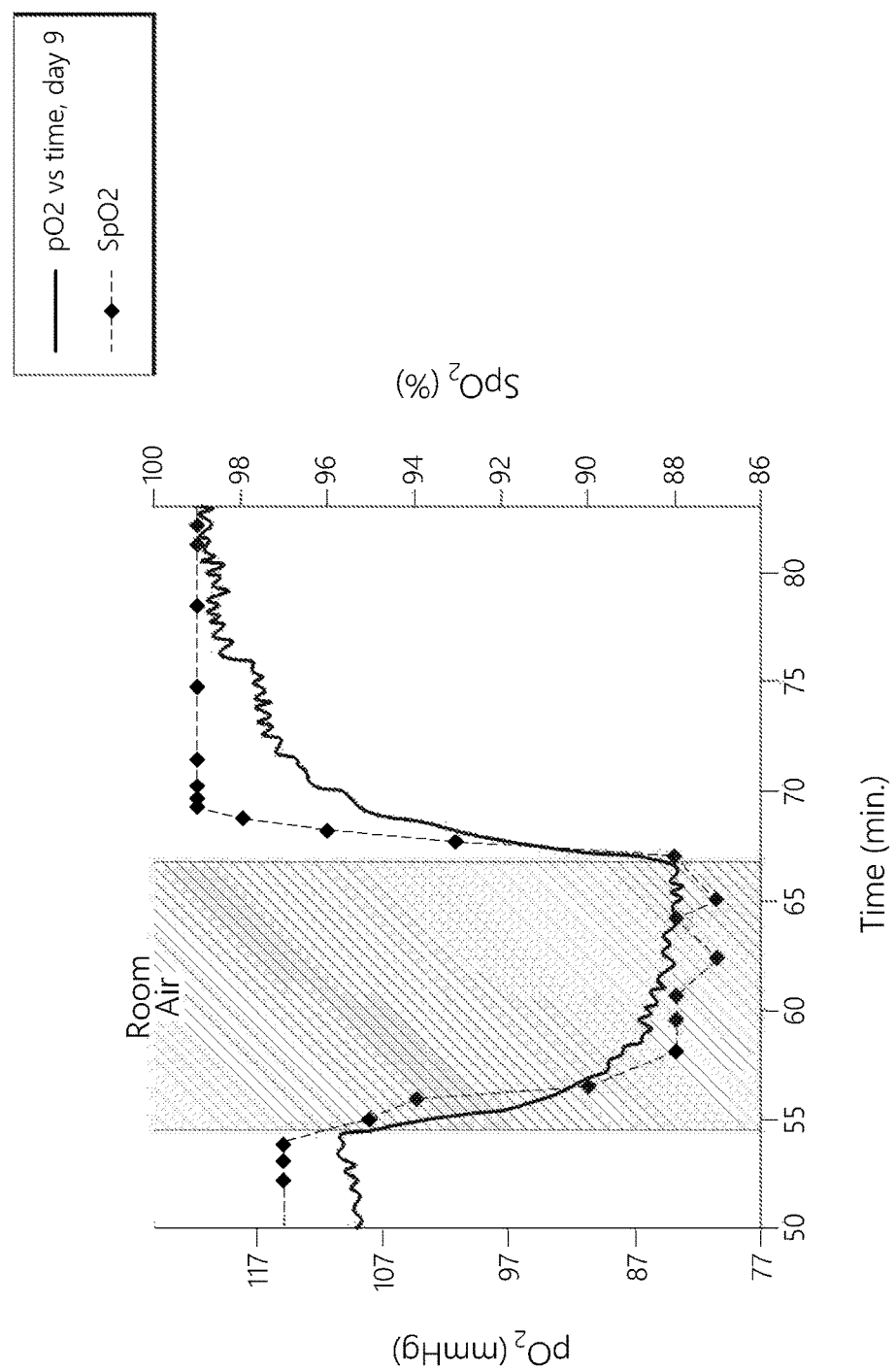
FIG. 7 shows continuous $pO_2$ measurements for embodiments of the disclosed implant.

The variable inhaled gas experiment was repeated for the same rate on day 9 (FIG. 7). Here pO$_2$ reaches steady state within the ~10 minutes of room air gas indicating rapid O$_2$ exchange between the beads and tissue as compared to day 5, an effect most likely mediated by tissue remodeling around the implant. As shown in FIG. 7, on day 9 pO$_2$ within capsules more rapidly moves towards a steady state (as compared to day 5) following the gas exchange.

FIG. 7 shows continuous pO$_2$ measurements taken by exciting the alginate beads with dye particles with light through rat skin and collecting the emitted light from the dye in the beads on a detector and calibrating that signal to pO$_2$ levels (full lines). The oxygen measured by the beads correlates with oxygen reported by a pulse-oximeter SpO$_2$ (dashed lines) when the rat breaths either 100% oxygen or 21% oxygen (room air). There is a delay due to physiologic differences in oxygen transport between arterial blood (pulse-ox SpO$_2$) and oxygen in the interstitial space where the sensor beads are implanted (bead pO$_2$).

Figure 8:
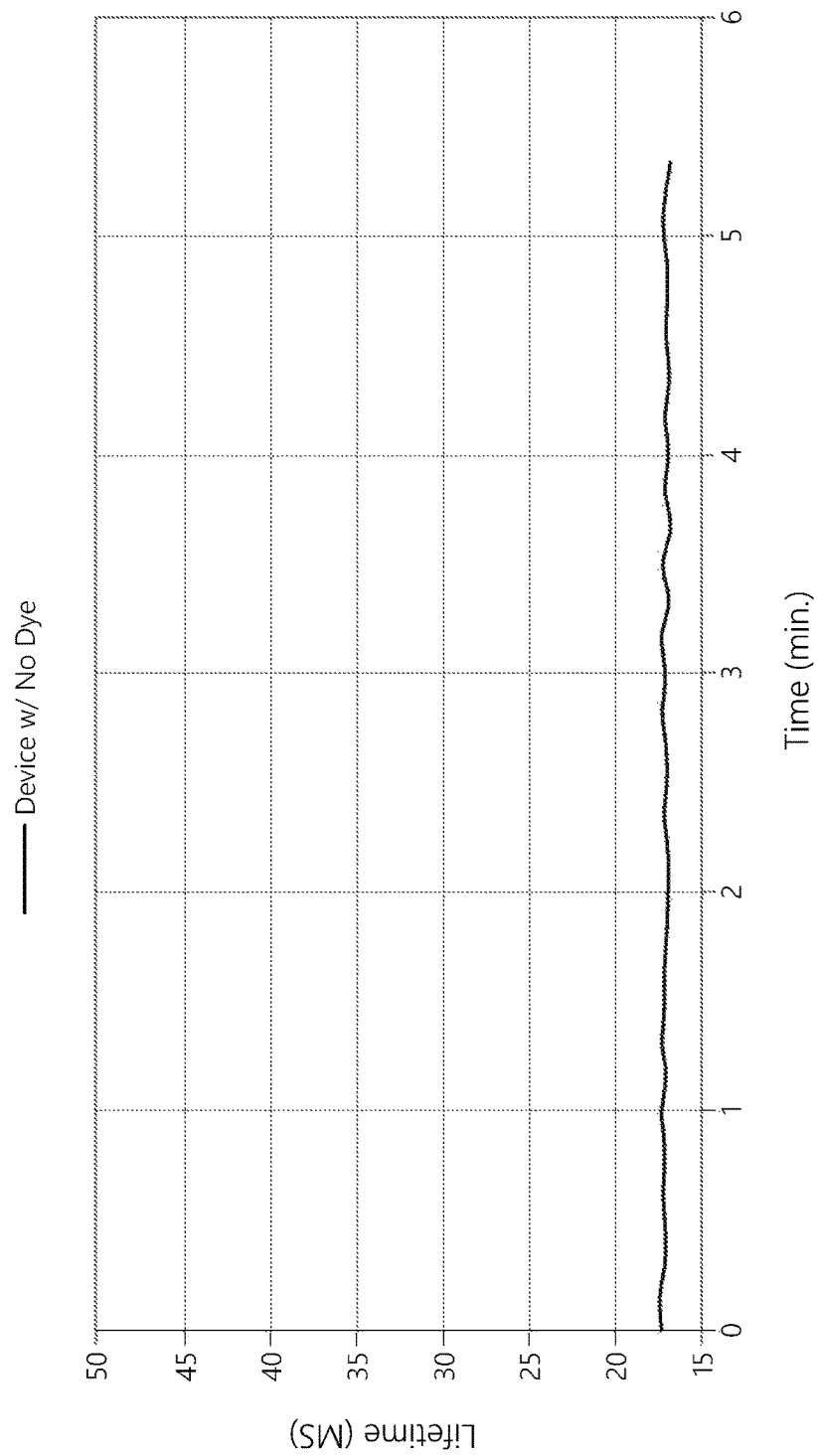
FIG. 8 illustrates a control embodiment of the disclosed implant with no dye.
Figure 9:
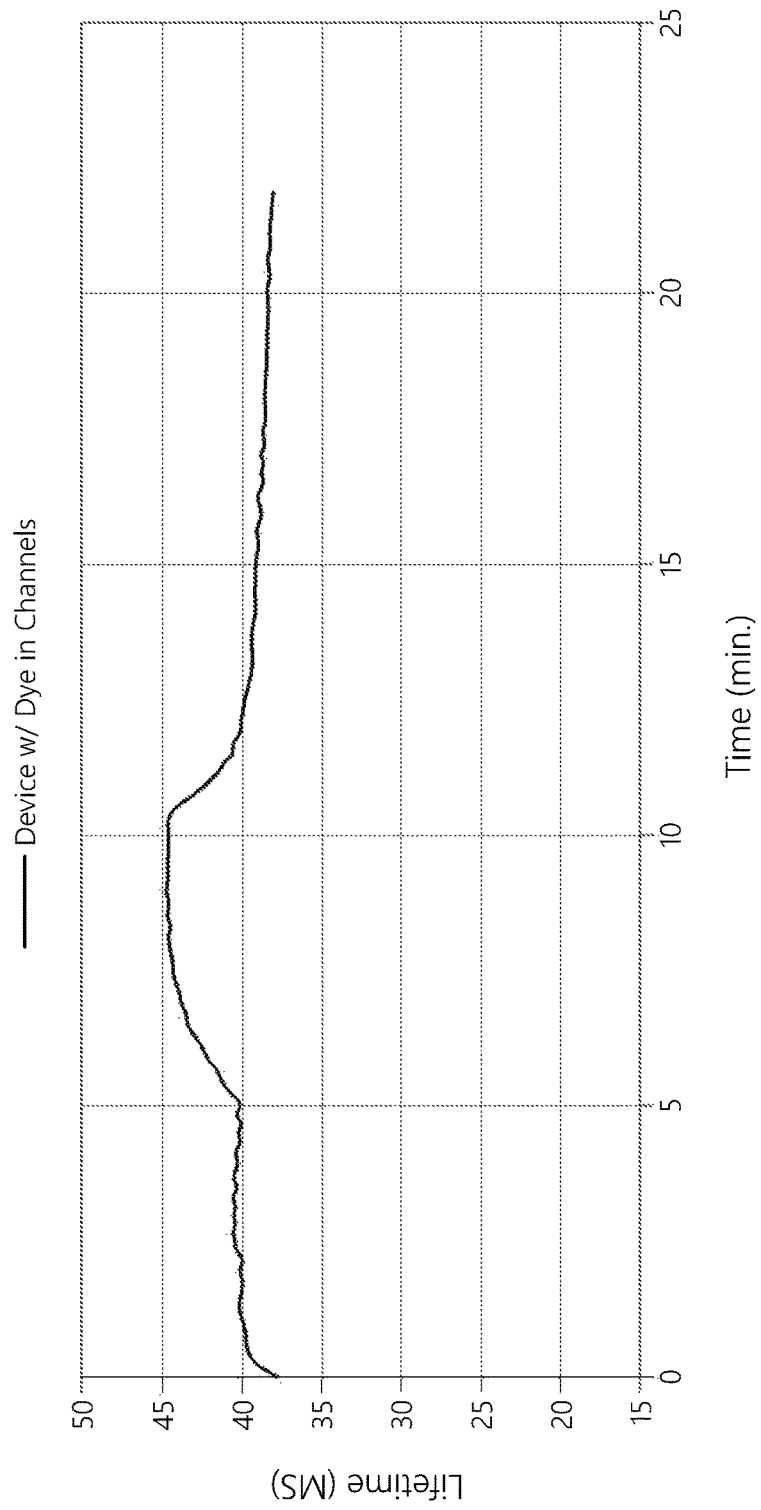
FIG. 9 illustrates testing results for an embodiment of the disclosed implant using dye.

FIGS. 8 and 9 illustrate the results of the dye injection in vitro. The dye was injected into channels of an embodiment of the device, and the channels were closed off, thereby isolating the dye within the channels. Accordingly, there is no perfusion or fluid flow between the outside and the inside of the device.

The device was then submerged in 1×PBS solution, and gas pumped into the solution. First, room gas was pumped into the solution, then Argon gas, then room gas. Accordingly, the only way for oxygen to enter the channels was through diffusion. Oxygen within the outside solution passes through the hydrogel via diffusion, entering the channels within the device, where the dye within the channels detect oxygen and have their fluorescent lifetime quenched.

FIG. 8 illustrates a control device with no dye in the device. First, room air was added into the PBS solution, followed by about 2 minutes of Argon gas, followed by about 3.5 minutes of room air. There is no oxygen-sensitive response as expected because the dye has not been incorporated.

FIG. 9 illustrates a device with the dye. First, room are was added into the PBS solution, followed by about 5 minutes of Argon gas, followed by about 10.5 minutes of room air. As shown, the lifetime fluorescence of the oxygen dye fluctuated based on the oxygen that entered into the system. The changes in oxygen were quickly detected, as the moment the gases were switched, the sensor detected the change in fluorescence lifetime.

Figure 10:
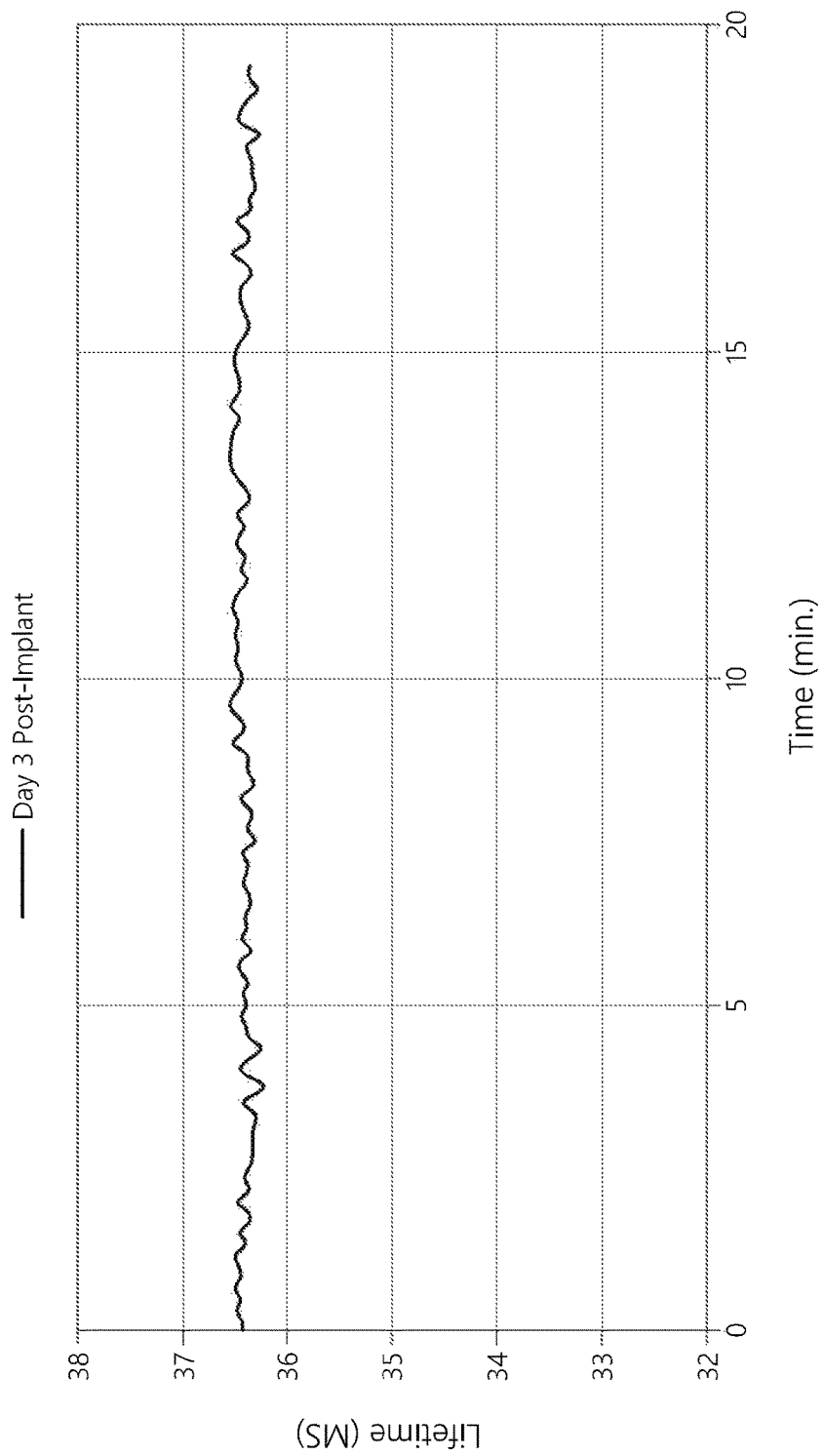
FIG. 10 illustrates testing results for an embodiment of an implant after 3 days.
Figure 11:
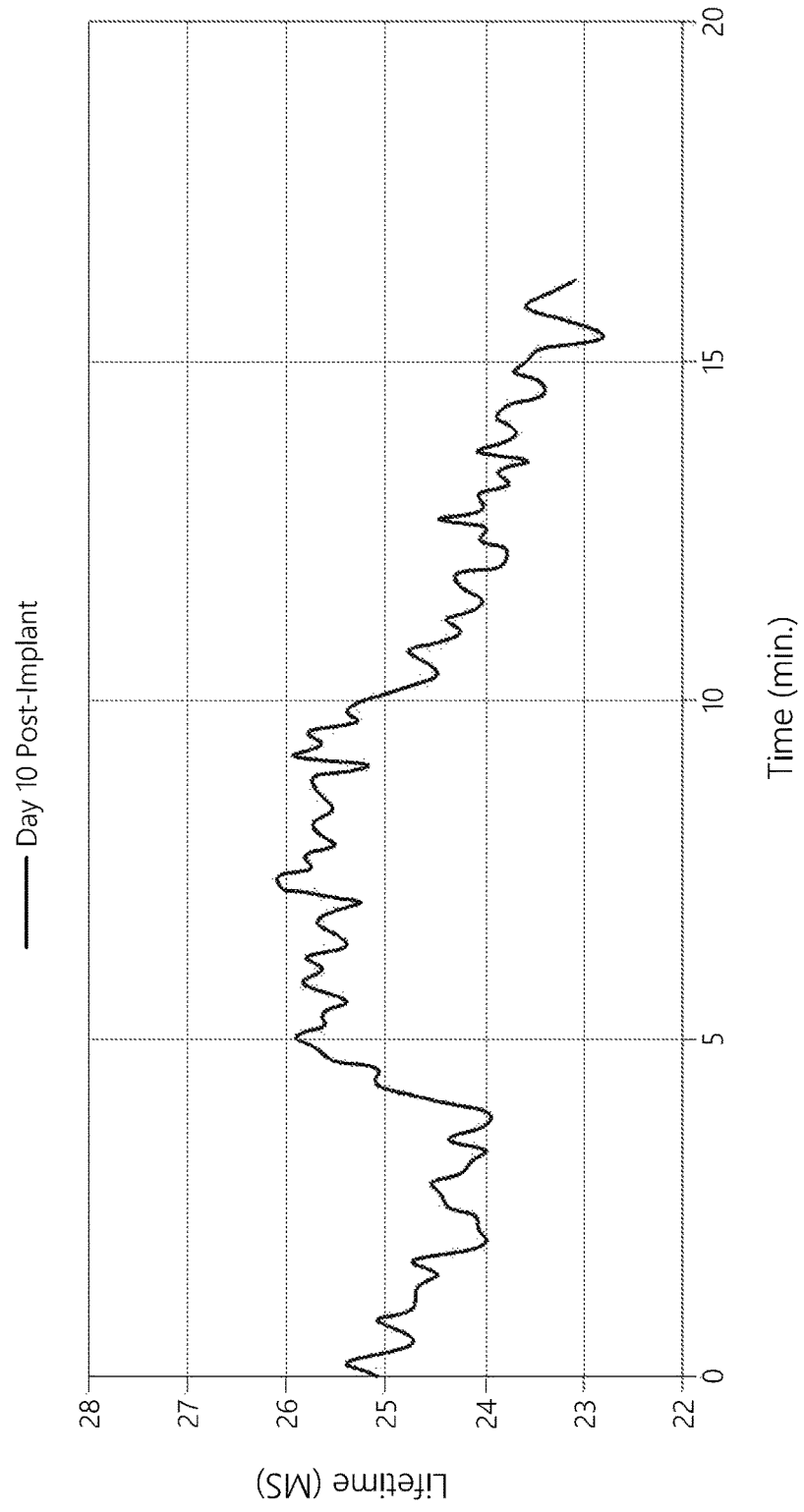
FIG. 11 illustrates testing results for an embodiment of an implant after 10 days.

FIGS. 10 and 11 illustrate in vivo testing using an oxygen dye. The injected dye was mixed with 1×PBS into the channels of the device, and the channels were sealed. A small incision was made on the dorsal skin of the Sprague-Dawley (SD) rate, where the device was implanted in the subcutaneous region adjacent the rodent's spine. Once implanted, the incision was stapled or sutured shut.

FIG. 10 illustrates day 3 post implant, with the fluorescent sensor placed on the skin of the rodent above the middle region of the implant. The rodent was breathing 100% oxygen initially, but changed to 60% oxygen at about 5 minutes, then back to 100% oxygen at about 12.5 minutes. As shown in FIG. 10, there are no dye dynamics detected. The vessels are still far from the implant, and there isn't enough vasculature invading the slit at this point because the wound is still healing. So applying changes to the amount of oxygen that the rodent is inhaling will not be detected by the dye because there is not enough vasculature in the slits of the device to carry oxygen that the dye will detect.

On the other hand FIG. 11 illustrates a day 10 post implant, with the sensor placed in the same position as in day 3. The rodent was initially breathing 100% oxygen, was changed to 60% oxygen at minute 3.5, and back to 100% oxygen at minute 9. As shown in FIG. 11, a dye dynamic correlating with the time at which a change in oxygen concentration that the rodent was inhaling occurred is detected. This indicates that the slits are vascularized and that the oxygen from this vasculature is diffusing through the walls of our device, into the channels of our device, where they are being detected by the dye housed within those same channels. A small change in lifetime may indicate arterial blood is near-by.

Figure 12:
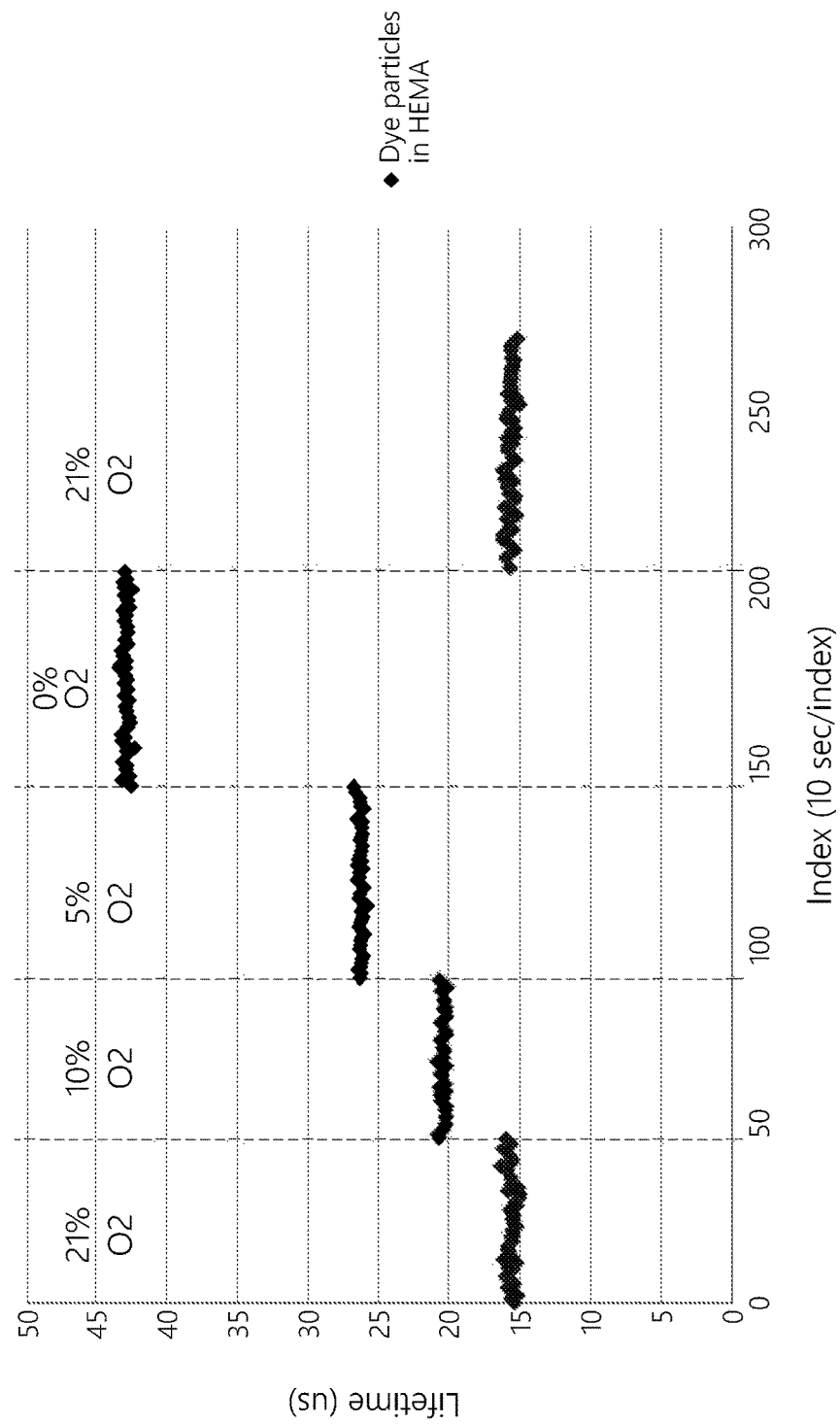
FIG. 12 illustrates $pO_2$ measurements for embodiments of oxygen sensitive dyes.

FIG. 12 illustrates results of further testing that was performed on the oxygen sensitive dyes. As above, the polymerized dye mixture was crushed into small particles, then the particles were mixed with a liquid HEMA/PEG mixture and the mixture was shaken with a vortex to disperse the particles throughout. Next, the dye/HEMA mixture was deposited onto a glass slide and polymerized. Measurements of $pO_2$ were then obtained by probing the particles that now lie in the Polymerized HEMA gel.

The dye particles in cured HEMA gel were tested in the lab for sensitivity to oxygen between 0-21% $O_2$ (no oxygen to room air quantity of oxygen) with calibrated gas mixtures. By exciting the dye particles with light and measuring their emitted light's lifetime decay as different concentrations of oxygen in calibrated gas mixtures was flowed over the cured HEMA/dye mixture, a calibration of dye lifetime values to oxygen concentrations could be made, as shown in FIG. 12.

Using a different matrix for the dye particles (alginate) lifetime values have been obtained that can be related to oxygen content from implanted gels loaded with dispersed dye particles in rats in vivo.

Method of Manufacturing OSMs

In some embodiments, an oxygen sensitive dye, such as, but not limited to, metalloporphyrin can be ground up into small particles (about 1-200 micron in diameter, though the size is not limiting) and mixed into a liquid synthetic or natural material, that can later be polymerized, or otherwise hardened into a gel or solid. The dye can be incorporated into the device through either of the manufacturing methods described above.

In some embodiments, platinum tetraphenyl tetrabenzoporphyrin (PtTPTBP) can be mixed with polystyrene and dissolved in chloroform. A thin sheet of the dye/polystyrene mixture can be formed by pipetting the liquid mixture onto a glass slide and allowing the solvent (the chloroform) to evaporate. Then a razor can be used to break the thin dye layer up into fine particles though other methods, such as ultrasound and sonication, can be used as well and the particular method is not limiting. These particles can then be added to a liquid hydroxyethylmethacrylate (HEMA)/polyethyleneglycol (PEG)/water/photoinitiator mixture and can be shaken to disperse the particles evenly throughout the liquid. The liquid/dye particle mix can then be pipetted onto a glass slide and cured under UV light for about 5 minutes.

From the foregoing description, it will be appreciated that embodiments of a sensor are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such steps need not be performed in the particular order shown or in sequential order, and that all steps need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

REFERENCES

All of the below references are hereby incorporated by reference in their entirety.

Baleizao, Carlos, et al. "Dual fluorescence sensor for trace oxygen and temperature with unmatched range and sensitivity." Analytical chemistry 80.16 (2008): 6449-6457.

Liebsch, Gregor, et al. "Luminescence lifetime imaging of oxygen, pH, and carbon dioxide distribution using optical sensors." Applied Spectroscopy 54.4 (2000): 548-559.

Wolfbeis, Otto S., et al. "Fiber-optic fluorosensor for oxygen and carbon dioxide." Analytical chemistry 60.19 (1988): 2028-2030.

Borisov, Sergey M., Roman Seifner, and Ingo Klimant. "A novel planar optical sensor for simultaneous monitoring of oxygen, carbon dioxide, pH and temperature." Analytical and bioanalytical chemistry 400.8 (2011): 2463-2474.

Ching C D et al. A reliable method for isolation of viable porcine islets. Arch Surg 136: 276-279, 2001.

Thanos C G and Elliot R B. Encapsulated porcine islet transplantation: an evolving therapy for the treatment of Type I diabetes. Expert Opin Biol Ther. 9(1):29-44. 2009

Sutherland D, et al. Isolation of human and porcine islets of Langerhans and islet transplantation in pigs. Journal of Surgical Research. 16(2): 102-111. 1974

Larsen M and Rolin B. Use of the Gottingen Minipig as a Model of Diabetes, with Special Focus on Type 1 Diabetes Research. ILAR Journal. 45(3):903-313. 2004

Korbutt G S, et al. Neonatal porcine islets as a possible source of tissue for humans and microencapsulation improves the metabolic response of islet graft post transplantation. Ann N Y Acad Sci. 831:294-903. 1997.

Lamb M et al. In vitro maturation of viable islets from partially digested young pig pancreas. Cell Transplant. 2013 Feb. 7.

Kuehn C et al. Young porcine endocrine pancreatic islets cultured in fibrin show improved resistance toward hydrogen peroxide. Islets. 2013 Nov. 21; 5(5)

Darrabie M D et al. Characteristics of poly-L-ornithine-coated alginate microcapsules. Biomaterials 26/34: 6846-6852, 2005.

de Vos P, et al. Multi scale requirements for bioencapsulation in medicine and biotechnology. Biomaterials. 90:2559-2570. 2009.

Schrezenmeir J. et al. Long-Term Function of Porcine Islets and Single Cells Embedded in Barium-Alginate Matrix. Horm Metab Res 1993; 25(4): 204-209

Chowdary K et al. Evaluation of Olibanum Resin as a new microencapsulating agent for Aceclofenac Controlled Release Microcapsules. 2(1) 0975-8585

Fehsel K et al. Necrosis is the predominant type of islet cell death during development of insulin-dependent diabetes mellitus in BB rats. 83(4):549-59.

Chang N et al. Direct Measurement of Wound and Tissue Oxygen Tension in Postoperative Patients. Annals of Surgery 197(4): 470-478.1983.

Spokane R B. et al. An implanted peritoneal oxygen tonometer that can be calibrated in situ. ASAIO Transactions. 36(3): M719-M722. 1990.

Schrenzenmeir J et al. Effect of microencapsulation on oxygen distribution in islet organs. Transplantation, 57 (1994).

Schrezenmeir, J et al. The role of oxygen supply in islet transplantation. Transp. Proc.
24(6): 2925-2929. 1992.

Michiels C. Physiological and pathological responses to hypoxia. 64(6): 1875-1882.

Veriter S, et al. In vivo selection of biocompatible alginates for islet encapsulation and subcutaneous transplantation. Tissue Eng Part A. 16(5):1503-1513. 2010.

Quaranta, Michela, Sergey M. Borisov, and Ingo Klimant. "Indicators for optical oxygen sensors." Bioanalytical reviews 4.2-4 (2012): 115-157.

Borisov S M et al. Phosphorescent Platinum (II) and Palladium (II) Complexes with Azatetrabenzoporphyrins—New Red Laser Diode-Compatible Indicators for Optical Oxygen Sensing. ACS Appl Mater Interfaces. 2010 Feb. 24; 2(2): 366-374.

Carraway, E. R.; Demas, J. N.; DeGraff, B. A.; Bacon, J. R. Anal. Chem. 1991, 63, 337-342.

Ladurner, Ruth, et al. "Predictive value of routine transcutaneous tissue oxygen tension ($tcpO_2$) measurement for the risk of non-healing and amputation in diabetic foot ulcer patients with non-palpable pedal pulses." Med Sci Monit 16.6 (2010): 273-277.

De Backer, Daniel, et al. "Monitoring the microcirculation in the critically ill patient: current methods and future approaches." Applied Physiology in Intensive Care Medicine 2. Springer Berlin Heidelberg, 2012. 263-275.

What is claimed is:

1. An implantable system for tissue, the system comprising:
   an implant configured to be inserted through a surface of a tissue and implanted entirely within a body portion of the tissue; and
   a plurality of oxygen-sensitive microparticles incorporated into the implant, the microparticles comprising a polymer or natural matrix and a radiation-sensitive dye embedded within the polymer matrix, wherein the radiation-sensitive dye is configured to emit an emission radiation upon excitation by a radiation source disposed on or above the surface of the tissue;
   wherein an intensity, a lifetime, or an intensity and a lifetime of the emission radiation correlates with oxygen levels within the implant.

2. The implantable system of claim 1, wherein the implant comprises a polymer.

3. The implantable system of claim 1, wherein the radiation-sensitive dye comprises porphyrin dye or a metalloporphyrin dye.

4. The implantable system of claim 1, wherein the radiation-sensitive dye is selected from the group consisting of platinum (II) meso-tetraphenyl tetrabenzoporphine and platinum (II) meso-tetra(pentafluorophenyl)porphine.

5. The implantable system of claim 1, wherein the polymer matrix comprises a polystyrene matrix.

6. The implantable system of claim 1, wherein the radiation sensitive dye is configured to interact with oxygen within the implant thereby quenching the emission radiation.

7. The implantable system of claim 1, wherein the implant comprises a portion made of a permeable material and the oxygen-sensitive microparticles are incorporated into the permeable material.

8. The implantable system of claim 1, wherein the implant comprises fluidic channels and the oxygen-sensitive microparticles are incorporated into the fluidic channels.

9. The implantable system of claim 1, wherein the implant comprises fluidic channels and the oxygen-sensitive microparticles are incorporated into the implant but not in the fluidic channels.

10. The implantable system of claim 1, wherein the implant further contains cells.

11. The implantable system of claim 10, wherein the cells are encapsulated islet cells.

12. The implantable system of claim 1, wherein the tissue is selected from the group consisting of patient tissue, animal tissue, plant tissue, and microbe culture.

13. The implantable system of claim 1, wherein the oxygen-sensitive microparticles are not sensitive to polyhydroxylated compounds.

14. A method of determining an oxygen concentration within an implant, the method comprising:
- deploying an implant entirely within a patient, the implant comprising:
  - a plurality of oxygen-sensitive microparticles comprising a polymer matrix and a radiation-sensitive dye embedded within the polymer matrix, wherein the radiation-sensitive dye is configured to emit an emission radiation upon excitation by a radiation source;
  - wherein an intensity, a lifetime, or an intensity and a lifetime of the emission radiation correlates with the oxygen concentration within the implant;
- irradiating the implant with the radiation source, the radiation source disposed outside of the patient, to excite the radiation-sensitive dye causing the radiation-sensitive dye to emit the emission radiation;
- detecting the intensity, the lifetime, or the intensity and the lifetime of the emission radiation; and
- determining the oxygen concentration within the implant based on the correlation between the emission radiation and the oxygen concentration.

15. The method of claim 14, wherein the oxygen concentration is determined continuously.

16. The method of claim 14, wherein the oxygen concentration is determined intermittently.

17. The method of claim 14, wherein the radiation-sensitive dye is selected from the group consisting of platinum (II) meso-tetraphenyl tetrabenzoporphine and platinum (II) meso-tetra(pentafluorophenyl)porphine.

18. A sensor system for determining oxygen concentration within an implant, the system comprising:
- an implant configured to be deployed into a patient, the implant having a plurality of oxygen-sensitive microparticles incorporated within, each of the plurality of oxygen-sensitive microparticles comprising a polymer matrix and a radiation-sensitive dye embedded within the polymer matrix, wherein the radiation-sensitive dye is configured to emit an emission radiation upon excitation by a radiation source; and
- an electro-optical probe configured as the radiation source and as a sensor to excite the oxygen-sensitive microparticles and detect the emission radiation from the radiation-sensitive dye, the electro-optical probe disposed outside of the patient;
- wherein an intensity, a lifetime, or an intensity and a lifetime of the emission radiation correlates with oxygen levels within the implant.

19. The sensor system of claim 18, wherein the radiation-sensitive dye comprises metalloporphyrin dye.

20. The sensor system of claim 18, wherein the electro-optical probe is located on the patient's skin, or near the patient's skin.

* * * * *